US009901655B1

(12) United States Patent
Archer et al.

(10) Patent No.: US 9,901,655 B1
(45) Date of Patent: *Feb. 27, 2018

(54) SYSTEM AND METHOD FOR PROVIDING AN AROMATHERAPY SHOWER

(71) Applicants: Sheri Ann Archer, Englewood, CO (US); Virgil Lee Archer, Englewood, CO (US)

(72) Inventors: Sheri Ann Archer, Englewood, CO (US); Virgil Lee Archer, Englewood, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/277,921

(22) Filed: Sep. 27, 2016

Related U.S. Application Data

(63) Continuation-in-part of application No. 15/249,368, filed on Aug. 27, 2016.

(51) Int. Cl.
| | |
|---|---|
| *A61L 9/04* | (2006.01) |
| *A61L 9/03* | (2006.01) |
| *A61L 9/02* | (2006.01) |
| *B05B 1/18* | (2006.01) |

(52) U.S. Cl.
CPC ............... *A61L 9/03* (2013.01); *A61L 9/02* (2013.01); *A61L 9/04* (2013.01); *B05B 1/18* (2013.01); *A61L 2209/13* (2013.01); *A61L 2209/15* (2013.01); *Y10S 239/11* (2013.01)

(58) Field of Classification Search
CPC .......... A61L 9/03; A61L 9/04; A61L 2209/15; A61L 2209/13; A61L 9/02; B05B 1/18; Y10S 239/11
USPC .......... 239/34, 289, 525, 530, 575, DIG. 11; 422/123
See application file for complete search history.

(56) References Cited

U.S. PATENT DOCUMENTS

| | | | |
|---|---|---|---|
| 7,975,936 B2* | 7/2011 | Paoluccio | B05B 7/0425 239/34 |
| 8,097,214 B2* | 1/2012 | Wood | A61L 9/122 422/123 |

* cited by examiner

*Primary Examiner* — Steven J Ganey
(74) *Attorney, Agent, or Firm* — Edwin H. Crabtree; Ramon L. Pizarro

(57) ABSTRACT

An aromatherapy ring made of soft, flexible silicon or like material. The ring includes a split ring body with an open trough therearound for receiving aroma liquid. The split ring body is adapted for wrapping around a shower filter or a shower head. The ring body includes first and second ends with magnets or like attaching means for engaging each other and holding the ring in a horizontal position on the shower filter or shower head. When warm or hot water passes through the shower filter or shower head, the aroma liquid is heated, thus providing a fragrance for aromatherapy, when taking a shower.

9 Claims, 2 Drawing Sheets

SYSTEM AND METHOD FOR PROVIDING AN AROMATHERAPY SHOWER

This non-provisional patent application is a continuation-in-part patent application based on a parent application Ser. No. 15/249,368, filed on Aug. 27, 2016, having a title of "Aromatherapy Ring for Shower Head", by Sheri Ann Archer.

BACKGROUND OF THE INVENTION

(a) Field of the Invention

This invention relates to a ring for holding aroma liquids and more particularly, but not by way of limitation, to a flexible, silicon, split ring adapted for wrapping around a shower filter or shower head and held thereon. The split ring includes a ring body having an open tray for holding an aroma liquid and providing a fragrance during a shower.

(b) Discussion of Prior Art

In U.S. Pat. No. 6,581,220 to Yekutiely et al., a method and apparatus for taking an aromatherapy shower is disclosed. The apparatus includes a conduit, a one-way valve, and a vacuum pump connected to a shower head and water supply. This complex shower pumping system is used to introducing an aroma liquid into a warm water stream. The subject invention eliminates the need for adding any plumping fixtures to the water supply of an existing shower.

SUMMARY OF THE INVENTION

In view of the foregoing, it is a primary objective of the subject invention to provide a simple, yet efficient, way of heating an aroma liquid during a shower and thus provide aromatherapy and fragrance, when taking a warm shower.

Another object of the invention is the ring includes a split ring body, which easily wraps around a portion of different types and sizes of shower filters or shower heads.

Still another object of the invention is the split ring body includes an open trough therearound, which can quickly be filled and refilled with aroma liquid.

The subject invention is an aromatherapy ring made of soft, flexible silicon or like material. The ring includes a split ring body with an open trough therearound for receiving aroma liquid. The split ring body is adapted for wrapping around a shower filter or a shower head. The ring body includes first and second ends with magnets or like attaching means for engaging each other and holding the ring in a horizontal position on the shower filter or shower head.

These and other objects of the present invention will become apparent to those familiar with shower filters and shower heads and the use of an aroma liquid when reviewing the following detailed description, showing novel construction, combination, and elements as herein described, and more particularly defined by the claims, it being understood that changes in the embodiments to the herein disclosed invention are meant to be included as coming within the scope of the claims, except insofar as they may be precluded by the prior art.

BRIEF DESCRIPTION OF THE DRAWINGS

The accompanying drawings illustrate complete preferred embodiments in the present invention according to the best modes presently devised for the practical application of the principles thereof, and in which.

DETAILED DESCRIPTION OF THE PREFERRED EMBODIMENTS

Figure 1:
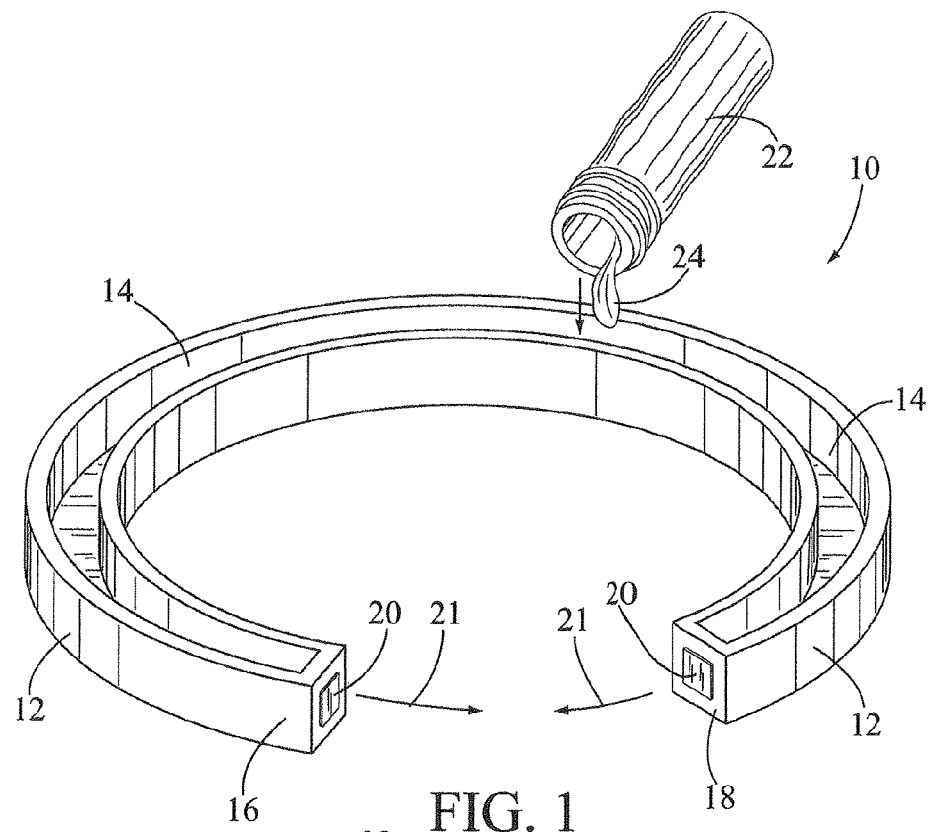
FIG. 1 is a perspective view of the subject aromatherapy ring with a split ring body and open trough. A container is shown pouring aroma liquid into the open trough.

In FIG. 1, a perspective view of the subject aromatherapy ring is shown having general reference numeral 10. The ring 10 includes a split ring body 12 with an open trough 14 therearound. The ring body 12 is made of a flexible, silicon or like material for ease in handling and cleaning. The body 12 is shown with a first end 16 and a second end 18. The ends 16 and 18 include magnets 20, embedded in the ends to prevent moisture from rusting the magnets. The magnets 20 are used for securing the ends together and closing the ring body, as shown by arrows 21. While the magnets are shown, it can be appreciated that various types of fasteners, not subject to be corroded by moisture, could be used equally well with the ring 10.

In this drawing, a container 22 is shown holding an aroma liquid 24 and pouring the liquid into the open trough 14.

Figure 2:
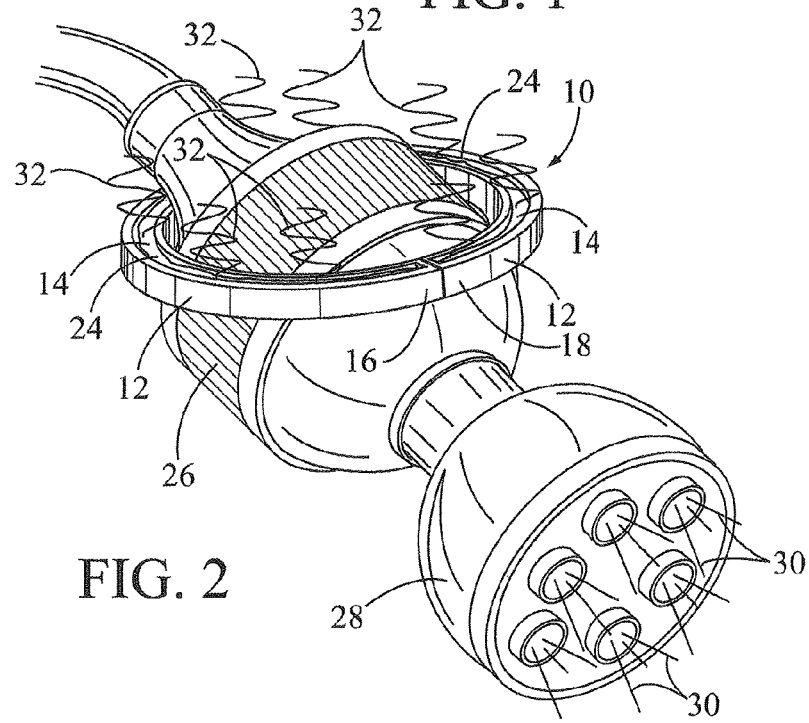
FIG. 2 is a perspective view of the ring received around a portion of a shower filter.

In FIG. 2, a perspective view of a shower filter 26 is shown attached to a shower head 28. In this drawing, the ring body 12 is shown received around a portion of a shower filter 26 and held thereon using the magnets 20 for securing the ends 16 and 18 together. It should be noted, the ring 10 is held in a horizontal position on the shower filter 26 so that the aroma liquid 24 does not spill out the open trough 14.

When warm water 30 or hot water passes through the shower filter 26 and out the shower head 28, the water heats the aroma liquid 24 in the trough 14. At this time, a fragrance 32 moves upwardly form the open trough for providing an aromatherapy shower.

Figure 3:
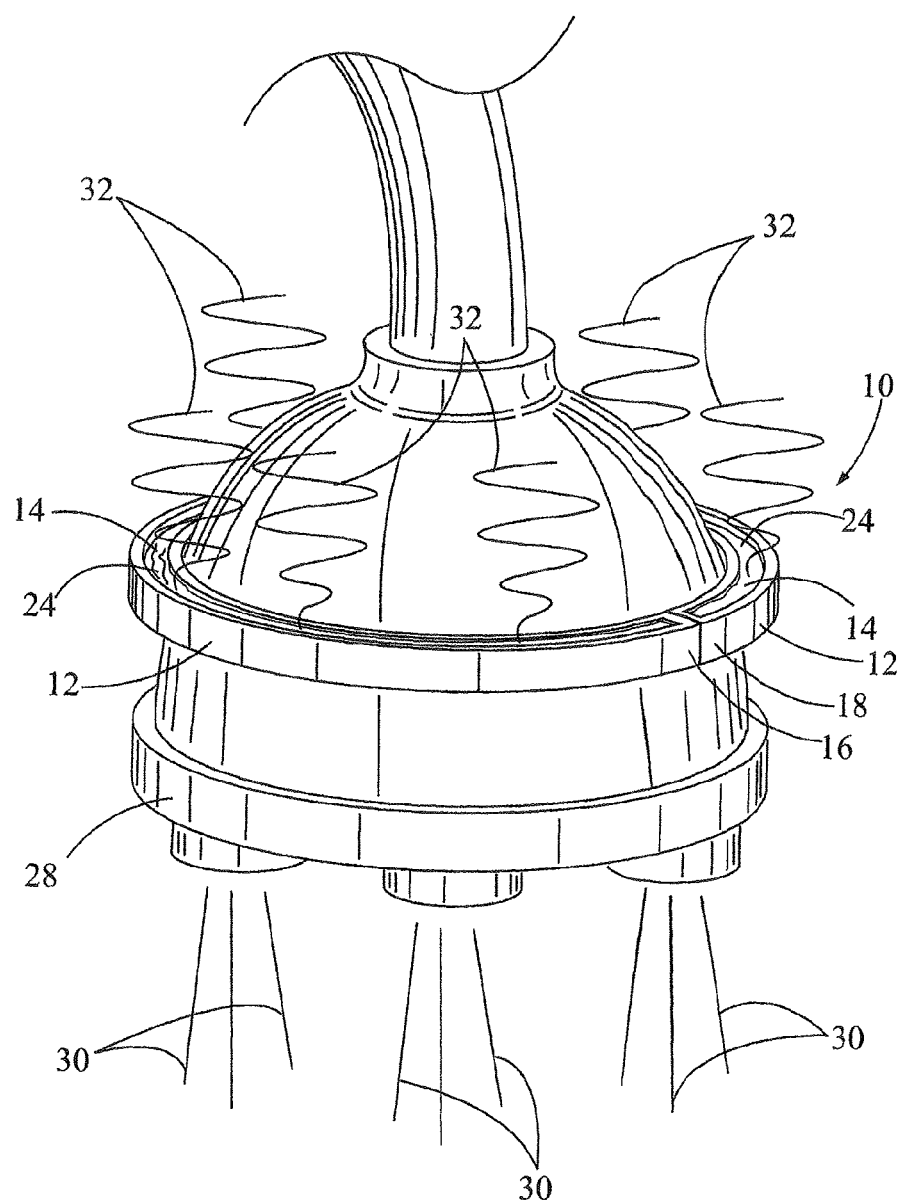
FIG. 3 is a perspective view of the ring received around a portion of a shower head.

In FIG. 3, another perspective view of the ring 10 is shown. In this drawing, the split ring body 12 is received around a portion of a shower head 28. Also shown in this drawing is the fragrance 32 moving upwardly from the heated aroma liquid 24 in the open trough 14.

While the above aromatherapy ring's structure and function has been discussed in detail, it should be kept in mind the ring 10 can be part of a system including the shower filter 26, shown in FIG. 2, or including the shower head 28, shown in FIG. 3.

Also, a method of taking an aromatherapy shower can be best described by first filling the open trough 14 of the split ring body 12 with the aroma liquid 24. The split ring body 12 is then wrapped around a portion of the shower filter 26 and attached using magnets 20, shown in FIG. 2. Also the split ring body 12 can be wrapped around a portion of the shower head 28 and attached using magnets 20, shown in FIG. 3.

The warm water 30 or hot water is then turned on in the shower. The warm water 30 passes through the shower filter 26 and through the shower head 28, thus heating the aroma liquid 24 in the trough 14 for providing an aromatherapy shower.

While the invention has been particularly shown, described and illustrated in detail with reference to the preferred embodiments and modifications thereof, it should be understood by those skilled in the art that equivalent changes in form and detail may be made therein without departing from the true spirit and scope of the invention as claimed except as precluded by the prior art.

The embodiments of the invention for which as exclusive privilege and property right is claimed are defined as follows:

1. A system for providing a aromatherapy shower, the system comprising:
   a split ring body with an open trough therearound, the open trough adapted for receiving aroma liquid therein, the split ring body including a first end and a second end;
   a first magnet mounted on the first end of the split ring body and a second magnet mounted on the second end of the split ring body; and
   a shower filter, the split ring body received around a portion of the shower filter and secured thereto using the first and second magnets.

2. The system as described in claim 1 wherein the magnets on the first end and on the second end of the split ring body hold the ring body in a horizontal position on the shower filter.

3. The ring as described in claim 1 wherein the ring body is made of a flexible silicon or like material.

4. A system for providing a aromatherapy shower, the system comprising:
   a split ring body with an open trough therearound, the open trough adapted for receiving aroma liquid therein, the split ring body including a first end and a second end;
   a first magnet mounted on the first end, of the split ring body and a second magnet mounted on the second end of the split ring body; and
   a shower head, the split ring body received around a portion of the shower head and secured thereto using the first and second magnets.

5. The system as described in claim 4 wherein the magnets in the first end and second end of the split ring body hold the split ring body in a horizontal position on the shower head.

6. The system as described in claim 4 wherein the ring body is made of a flexible silicon or like material.

7. A method for providing a aromatherapy shower in a shower with warm or hot water, the method steps including:
   filling an open trough in a split ring body with aroma liquid, the split ring body including a first end and second end;
   placing the split ring body around a portion of a shower filter or a shower head; therein,
   securing the split ring body around the portion of the shower filter or the shower head using a first magnet mounted on the first end of the split ring body and a second magnet mounted on the second end of the split ring body; and
   turning on the warm or hot water to the shower and heating the aroma liquid in the open trough, thus providing an aromatherapy shower.

8. The method as described in claim 7 wherein the magnets in the first end and second end of the split ring body hold the ring body in a horizontal position on the shower filter or the shower head.

9. The method as described in claim 7 wherein the ring body is made, of a flexible silicon or like material.

* * * * *